US006699293B2

(12) United States Patent
White

(10) Patent No.: US 6,699,293 B2
(45) Date of Patent: *Mar. 2, 2004

(54) PROSTHESIS HAVING WEDGE-SHAPED BODY

(75) Inventor: Patrick Michel White, Mahwah, NJ (US)

(73) Assignee: SCT Incorporated, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/164,764

(22) Filed: Jun. 7, 2002

(65) Prior Publication Data

US 2002/0151984 A1 Oct. 17, 2002

Related U.S. Application Data

(62) Division of application No. 09/040,700, filed on Mar. 18, 1998, now Pat. No. 6,428,578.

(51) Int. Cl.[7] .................................................. A61F 2/36
(52) U.S. Cl. ................................. 623/23.22; 623/22.42
(58) Field of Search ........................... 623/18.11, 19.11, 623/21.11, 22.41, 20.34, 20.36, 22.42, 22.43, 23.15, 23.14, 23.18, 23.34, 23.35, 23.46, 23.47, 23.22, 23.23

(56) References Cited

U.S. PATENT DOCUMENTS

| 5,858,020 A | * | 1/1999 | Johnson et al. | 623/23 |
| 5,876,459 A | * | 3/1999 | Powell | 623/18 |
| 6,428,578 B2 | * | 8/2002 | White | 623/23.22 |

* cited by examiner

Primary Examiner—Bruce E Snow
(74) Attorney, Agent, or Firm—Klauber & Jackson

(57) ABSTRACT

A modular orthopedic prosthesis has a body with a generally triangular cross-section near one end, allowing its angular corners to bite or incise into the surrounding bone cavity for rotational stability. A stem, which may be either unitary or modular in structure, is received within a through-bore of the body, having a proximal neck and distal shaft. A connecting sleeve receives the stem and is, in turn, received within the bore of the body, then actuated to lock the stem and body together.

10 Claims, 9 Drawing Sheets

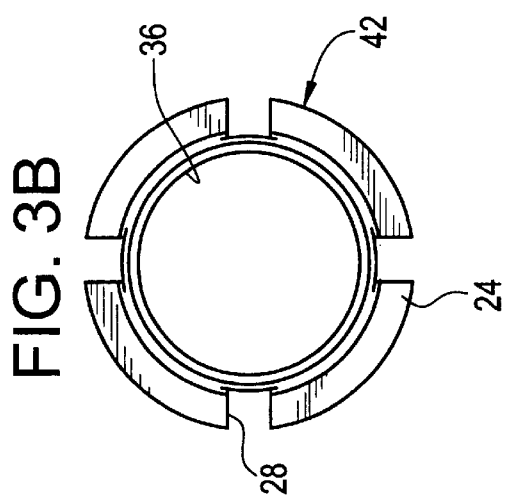
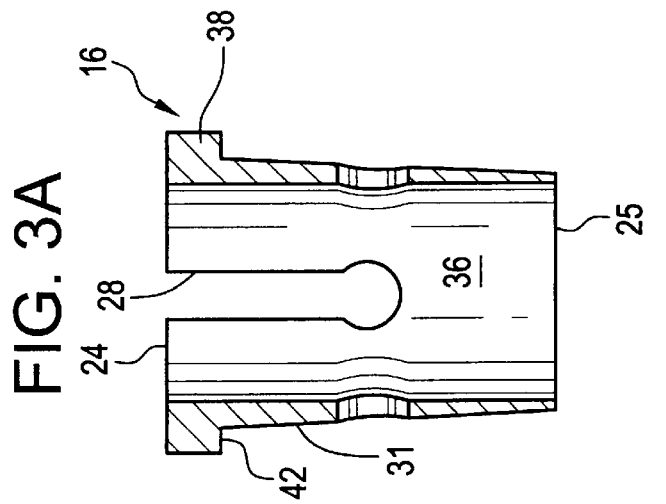
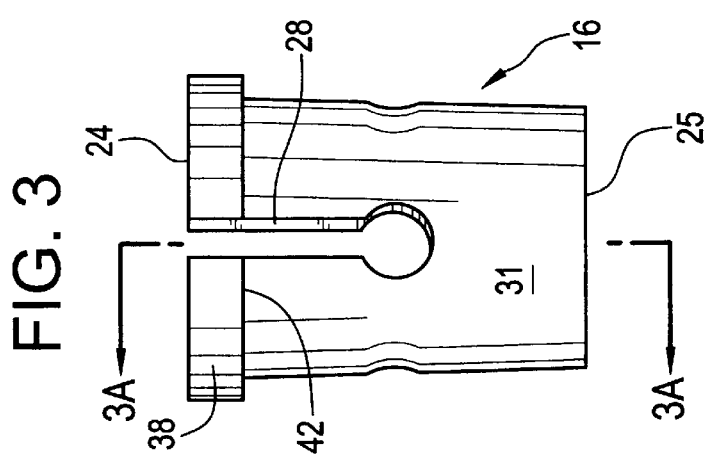

PROSTHESIS HAVING WEDGE-SHAPED BODY

RELATED APPLICATION

This application is a division of application Ser. No. 09/040,700 filed Mar. 18, 1998 U.S. Pat. No. 6,428,578.

TECHNICAL FIELD

This invention relates generally to orthopedic prosthesis, particularly to those having a modular construction that is assembled from selected components and implanted during re-constructive arthroplastic surgery.

BACKGROUND

It is know that bone matter that is not stressed/loaded will atrophy and lose viability, a problem which currently persists in present orthopedic implants.

One approach others have taken is to provide a collar intended to correspond in shape and size to the prepared cavity of a proximal femur, ostensibly to offer rotary stability to the implanted device. For example, U.S. Pat. No. 4,790,852 to Noiles shows a modular hip prosthesis including a collar having a shape with a keyhole cross-section and terraces surrounding the outer surface perpendicular to the longitudinal axis of the collar. The collar has a tapered proximal-to-distal contour. However, the shape of the collar is instead dictated by the milling instrumentation used to prepare the proximal femoral cavity. According to the procedure, a surgeon resects the femoral head (ball) with an osteotome, thereby exposing the medial aspect of the cavity, then reams the intramedullary canal to make a space for the collar. The medial bone cavity is then milled to make it fit set criteria of the implant. U.S. Pat. No. 5,002,578 to Luman also has transverse terraces and a supposed cavity conforming cross-section. However, such terraces, like those of the above Noiles '852 patent, do not counteract rotary motion of the prosthesis, but rather axial motion. U.S. Pat. No. 4,549,319 to Meyer has an external geometric pattern of elongated projections spaced circumferentially on a hip prosthesis. U.S. Pat. No. 4,624,673 to Meyer discusses a component for use in a prosthetic joint having a hollow tube with a closed end and an open end. The area of the external surface adjacent to the open end is at least twice the area of the external surface adjacent to the closed. A plurality of terraces, oriented orthogonal to a distal shaft, are on the external surface. A female part of self-locking taper is provided to connect the components. U.S. Pat. No. 4,846,839 to Noiles shows a modular hip with a collar having an oval cross-section and a terraced external surface, connecting with a stem. Products have been marketed generally based upon this approach, e.g., The SROM Hip, of Joint Medical Products, Inc.

The aforementioned patents seek to provide rotatory stability by circumferential contact between the prepared femoral cavity and an outer surface of a main body or collar member. This type of contact is actually tangential in nature. The use of an oval cross-sectional shape often does not allow the outer surface of the prosthesis collar to effectively engage the intact bone. In many cases, especially in revision patients, healthy bone can be problematic to uniformly contact, for example, in the lateral aspects of the proximal femur, where the greater trochanter is left largely undisturbed by the surgeon during a primary implantation. The lack of rotatory stability, needed for uniform stress on such healthy bone, can cause the intact tissue to weaken and possibly atrophy, unacceptably, at some point following the initial implantation of the prosthesis.

Others, including some of the above approaches, have further sought to achieve prosthesis-cavity conformance while providing various modular constructions and ways of connecting the components of the prosthesis.

For example, related U.S. Pat. Nos. 5,370,706 and 5,080,685 to Bolesky show a body member having a neck with a base defining a neck basal plane. A body member includes an upwardly and inwardly directed portion and a tapered longitudinal bore. A tapered connector engages a head member with the upwardly and inwardly directed portion. A problem experienced with this particular design is its limited strength, due to the location of the interconnecting components. Thus, the point of connection of the shaft must bear a load that is often too great, without being able to distribute that force. In U.S. Pat. No. 4,878,917 to Kranz, et al., there is shown a modular implant with a tensioning connector rod structurally designed to break when loaded a selected amount. U.S. Pat. No. 5,201,882 to Paxson discloses indicia for selecting the desired ante-version of a modular hip stem that is connected via tapered fittings to a unitary neck/body member, but the neck is not independently adjustable relative to the body. U.S. Pat. No. 5,725,592, issued to the present inventor, describes a modular hip prosthesis having a distal stem component that connects with a body component and a neck component both having tapered throughbores.

There is still a need for a modular prosthesis having independently adjustable components, and for a connector mechanism allowing the surgeon to visibly adjust them. Also, a prosthesis is needed, having an adjustable body with a geometry that incisively engages healthy bone, then securely locks with a stem component inter-operatively. The prior patents do not show a body shape capable of adjustably engaging healthy bone tissue in such a manner.

Other prior unitary implants have had various shapes, but the distal shaft and main body portions of these were not independently adjustable components, allowing surgeons to inter-operatively achieve optimal engagement of the body with healthy bone tissue.

Moreover, a need exists for a prosthesis that allows the surgeon to independently adjust the implant and realize the aim of engaging intact bone, as well, for an implant geometry that incises the intact bone and stresses it.

There is a further need for a modular implant that is infinitely adjustable, rotationally and axially, using a relatively simple array of components, allowing a surgeon flexibility while reducing the cost of carrying a large inventory of sizes. Such a need also exists while continuously delivering desired benefits, via the implant geometry, to a patient's intact bone. A modular implant design is called for, whose components can be readily assembled inter-operatively and securely locked together by the surgeon to achieve these purposes.

SUMMARY OF THE INVENTION

According to the invention, there is provided a modular orthopedic prosthesis including a stem having one end with an elongated portion and another, longitudinally opposed end with a first means presenting a joint motion surface. The prosthesis has a body including a bore defining at least a first axis and having a polygonal cross-section with at least two angular corners adapted to bite or incise into the bone cavity of a patient to prevent rotation of the implanted prosthesis relative to the bone. Means are provided for connecting and locking the stem and body together in a fixed position.

In a preferred embodiment of this invention, the body has a first end with a generally triangular cross-section in the region of the first end and a generally round cross-section in the region of its second end, presenting a multi-axial wedge shape.

According to the invention, in another of its aspects, a modular orthopedic prosthesis is provided. The prosthesis comprises a stem component having one end with an elongated portion and another, longitudinally opposed end with a first means presenting a joint motion surface. A body component includes a bore defining at least a first axis. A radially expansible sleeve has opposed ends, one end received within the bore and the other end projecting outwardly from the bore, the sleeve adjustably connecting the stem and body together and locking them in a fixed position.

In a preferred embodiment of this invention, the joint motion surface is adjustably spaced from the body.

An advantage of the present invention is inventory and manufacturing cost savings, since its modularity allows for economy in manufacturing, as any number of well-known stem types may be selected, and also reduces the inventory of pieces needed on-hand for each surgical procedure.

Another advantage of the invention is enhanced clinical benefits, as the wedge shape offers enhanced rotatory stability of the prosthesis in use, particularly with revision surgery patients.

A further advantage of the invention is in providing a connector mechanism that is highly secure once fixed in place, meanwhile providing the surgeon inter-operative flexibility to axially and rotationally adjust the stem independently of the body.

A still further advantage of the invention gives a surgeon the capability to rotationally "dial" the body in order to have its triangular corners contact and "bite into" or incise as much available healthy bone as possible. By evenly loading/stressing such intact bone, wherever found by the surgeon, particularly in revision patients, it is possible to avoid potential eventual atrophy of the bone tissue.

Other objects and advantages will become apparent to those skilled in the art by reference to the following Description and Drawings.

BRIEF DESCRIPTION OF THE DRAWINGS

FIG. 3 is an external side view of the sleeve component of the present invention, taken from either an anterior-posterior or medial-lateral aspect;

FIG. 3A is a longitudinal section of the body of FIG. 3, taken substantially along the lines 3A—3A;

FIG. 3B is an external top view of the proximal portion of the sleeve of FIG. 3;

DETAILED DESCRIPTION

Figure 1:
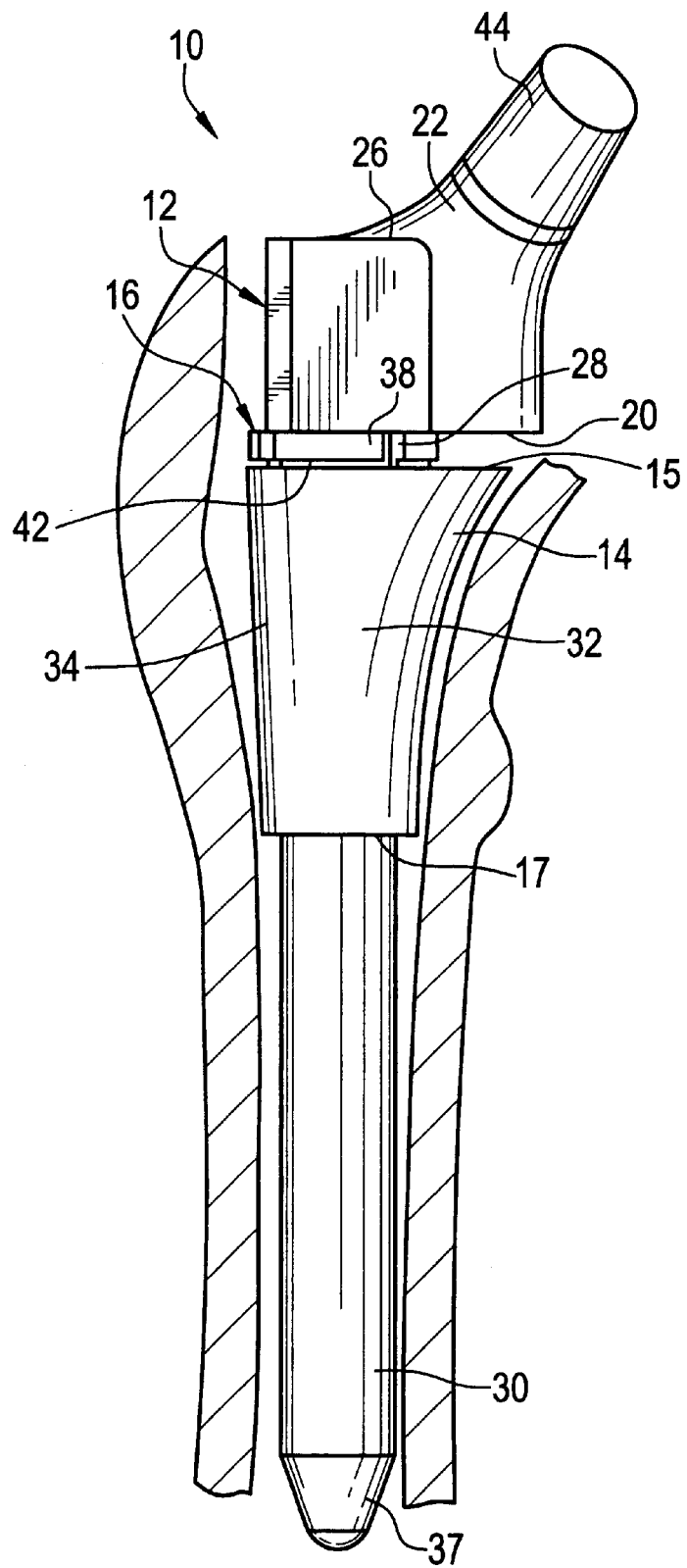
FIG. 1 is a perspective view of a modular hip prosthesis of the invention, fully assembled and implanted in a proximal femur, with the bone longitudinally cut away.
Figure 2A:
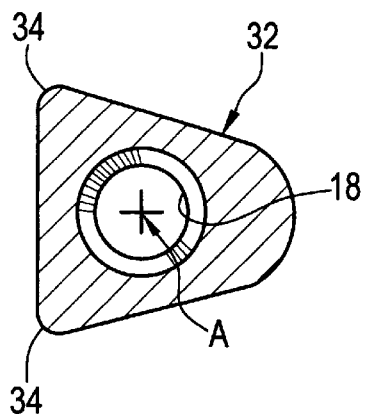
FIG. 2A is a cross-section of the proximal portion of the body of FIG. 2, taken substantially along the lines 2A—2A.
Figure 2:
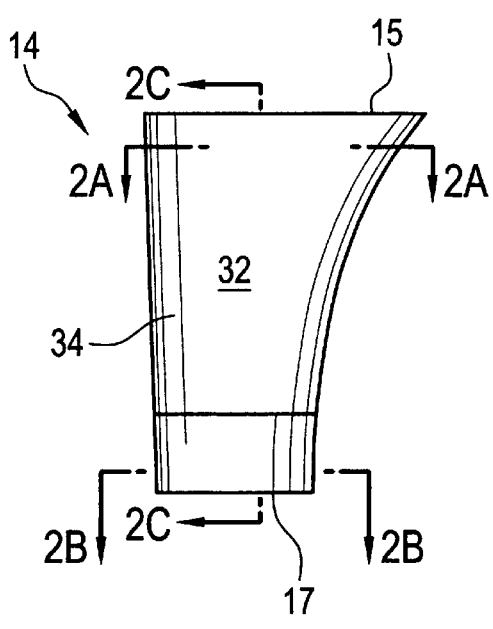
FIG. 2 is an external side view of the body component of the present invention, taken from an anterior-posterior aspect.
Figure 2C:
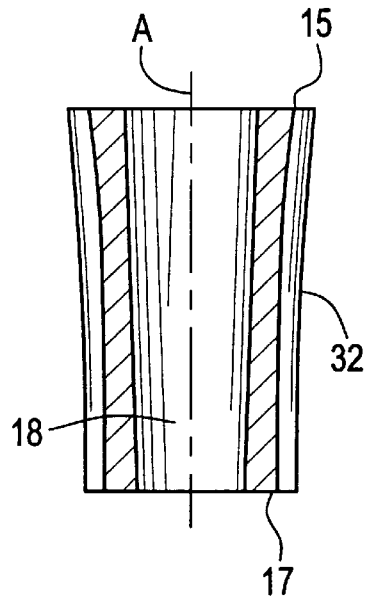
FIG. 2C is a cross-section of the proximal portion of the body of FIG. 2, taken substantially along the lines 2C—2C.
Figure 2B:
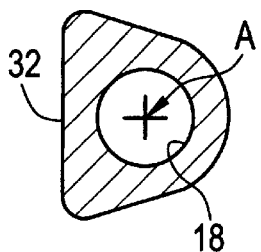
FIG. 2B is a cross-section of the proximal portion of the body of FIG. 2, taken substantially along the lines 2B—2B.
Figure 4:
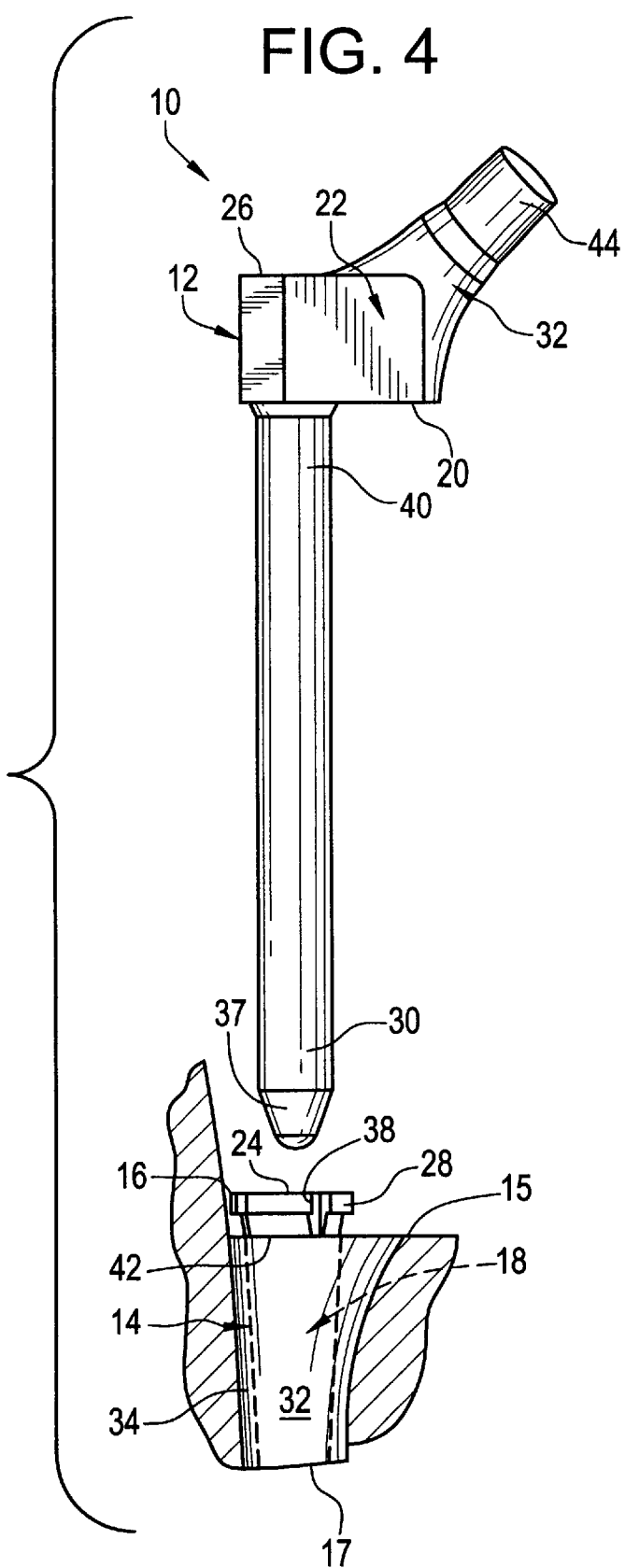
FIG. 4 is a partially exploded perspective view of the invention, showing the sleeve partially seated in the bore of the body, prior to insertion of the stem.
Figure 6:
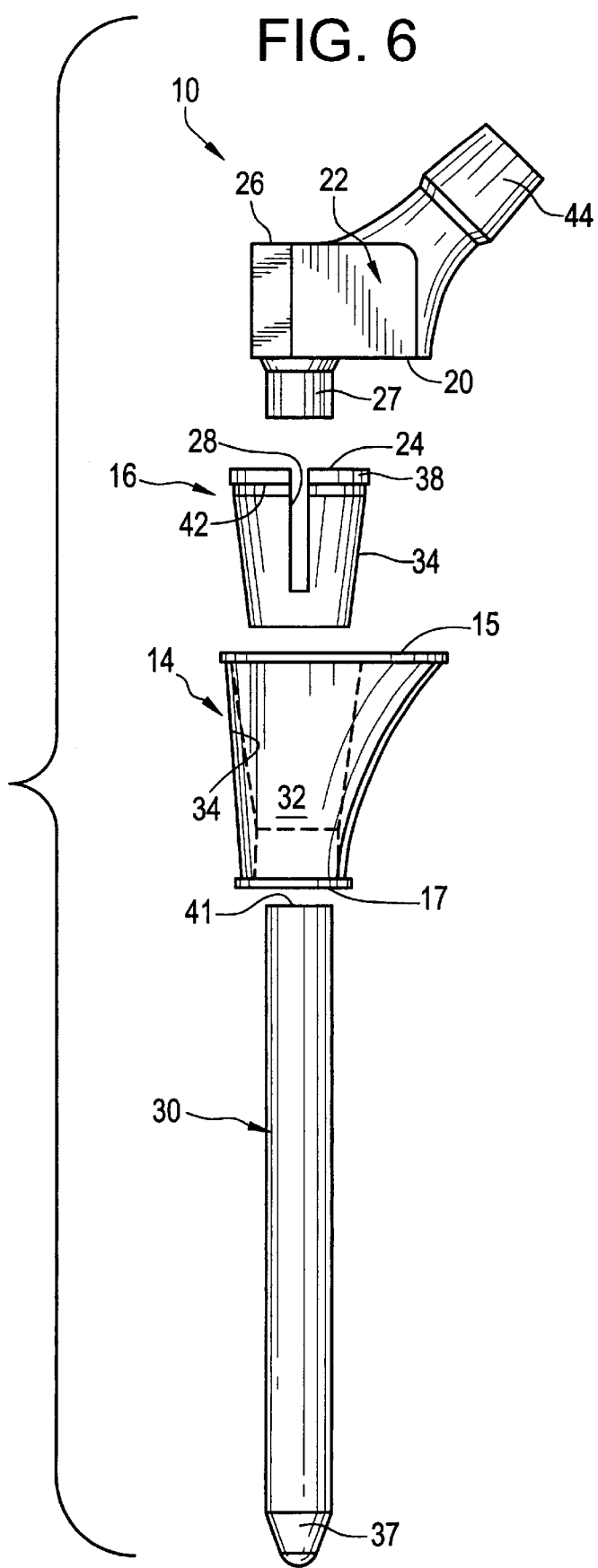
FIG. 6 is an exploded perspective view of the stem, body and sleeve of the invention, shown prior to assembly, wherein the stem has a modular construction with separate neck and distal shaft components.
Figure 7:
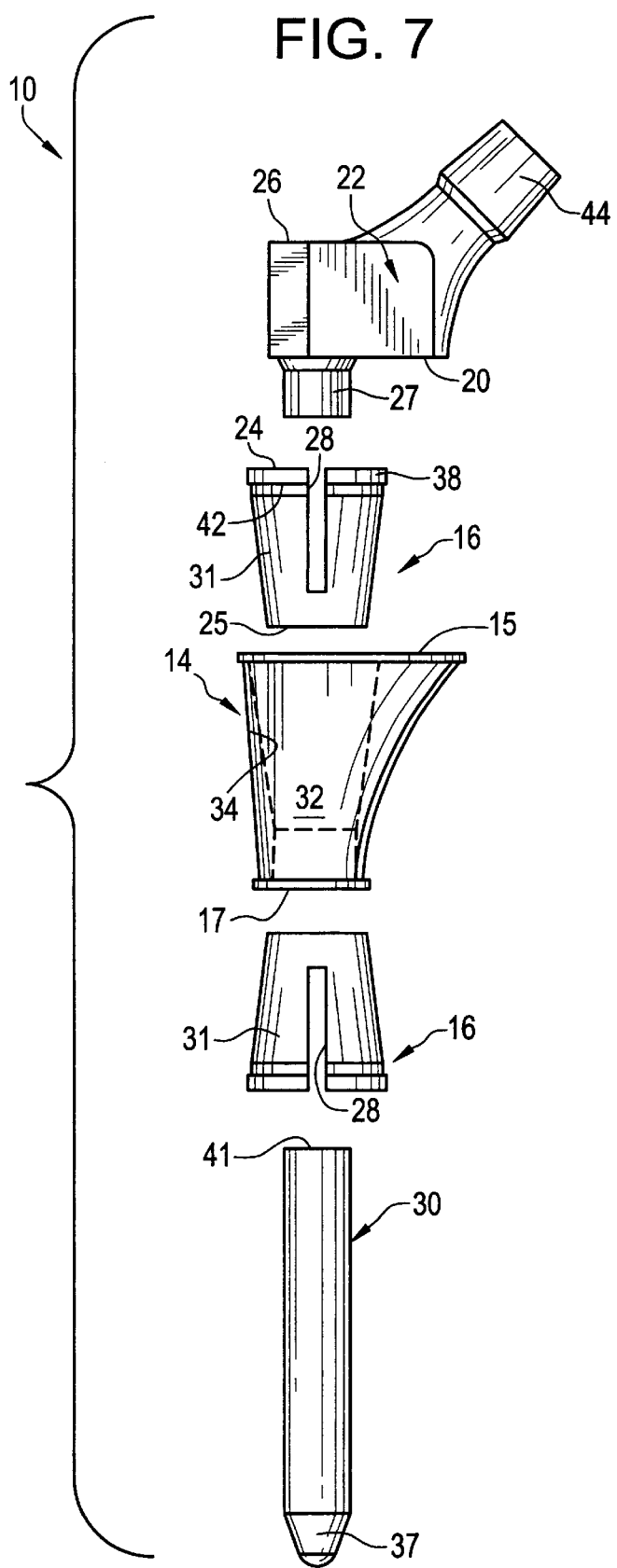
FIG. 7 is an exploded perspective view of the prosthesis of FIG. 6, showing the distal shaft component of the modular stem being connected to the body with another independent sleeve.
Figure 8:
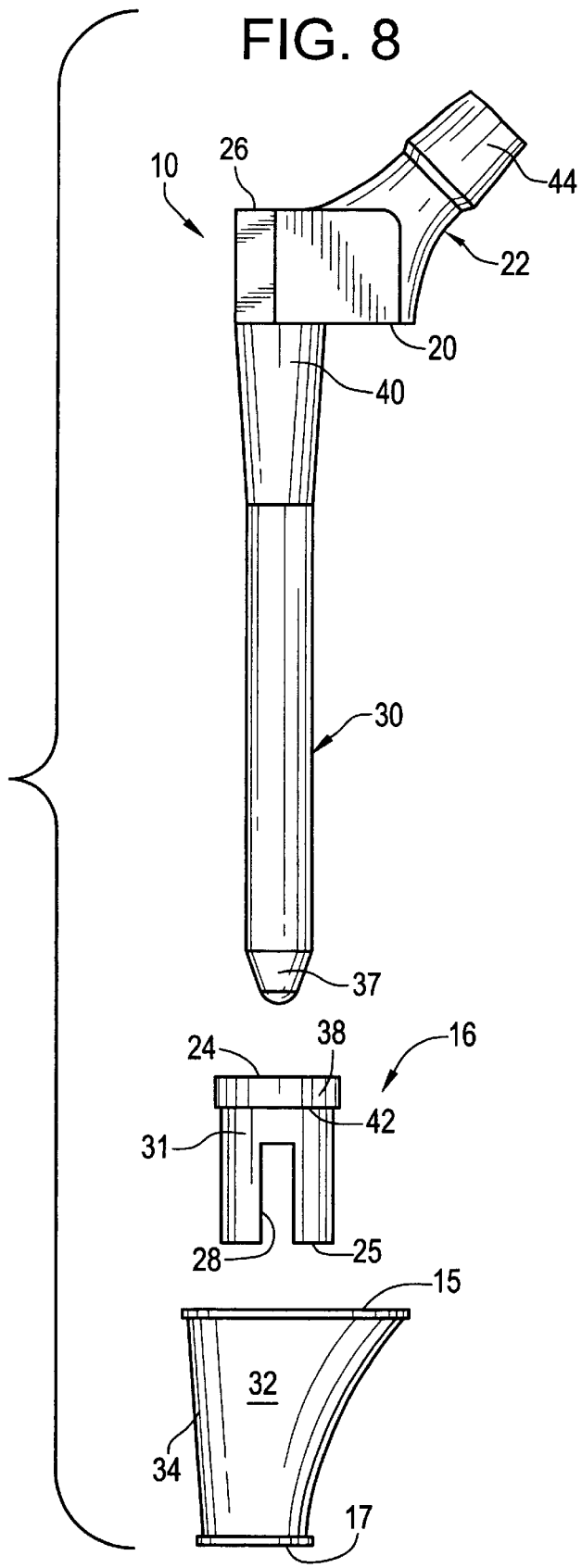
FIG. 8 is an exploded perspective view of the prosthesis of the invention showing a unitary stem with a tapered connection region, a sleeve with a cylindrical outer surface and a tapered internal bore, and a body with a linear through-bore.

According to the invention, as shown in FIGS. 1–13, there is provided a modular prosthesis assembly, generally shown at 10, including a stem component, generally shown at 12, a body component, generally shown at 14, and means in the form of a sleeve, generally shown at 16, for affixing the stem and body together. In FIGS. 1, 4, and 8 the stem 12 is a unitary member, however, as shown in FIGS. 6–7, the stem can be in a modular form. In FIGS. 1, 4, 6 and 8, the prosthesis 10 comprises a single sleeve, however, as shown in FIG. 7, the prosthesis can include a pair of sleeves 16 in conjunction with a modular stem. Nevertheless, a single sleeve is preferred. In FIGS. 1, 2, 2-C, 4, and 6–13, the body has a first or proximal end 15 and a second, longitudinally opposed or distal end 17. The body 14 functions as a wedge generally in the anterior-posterior and medial-lateral plane, as well as the proximal-distal plane, as will be herein elucidated.

The body 14 has a bore 18 with a first axis A extending between the proximal 15 and distal 17 ends, through which stem 12 is received, once the stem has been passed through sleeve 16. The assembled stem 12 and sleeve 16 are seated in bore 18 and, as they are urged into the bore fully, the sleeve radially compresses to pressure-lock the stem and body together in a fixed relative position.

The present invention employs a distinctive geometry and connection technology that variably locks together the three fundamental components 12, 14 and 16 of the prosthetic hip 10 into a fixed configuration. In surgery, the proximal femoral bone cavity is prepared by reaming and then a finish broaching operation, thereby creating the desired cavity in the bone. In FIG. 4, the sleeve 16 is placed in the bore 18 (phantom) through a first end 15 of body 14 but left proud, i.e., not fully seated in the bore. Then stem 12 is passed through the sleeve 16 until the desired neck height is achieved for restoring the tension of the total articulated joint. Indicia could be added to allow visual recognition of the height adjustment by the surgeon. Once the proper height is achieved, an axial force is applied to the top 24 of sleeve 16, locking it against the bore 18. In a preferred embodiment, axial force can be applied to the top 26 of neck 22 and transmitted indirectly, through the bottom 20 of neck 22, to top 24 of sleeve 16. The components are actuated and locked together in this manner as shown by FIGS. 1 and 4, in the case of a unitary stem 12, and similarly in the case of a modular assembly. As shown in FIGS. 6–7, modular neck 22 has a protrusion 27 extending distally from bottom 20 of the neck for connecting with sleeve 16. Protrusion 27 may be either straight or tapered, depending upon the geometry of its interconnecting member.

The sleeve 16 will now be more particularly described. Preferably, sleeve 16 is radially flexible by means of a preferred split collet 28, as shown in FIGS. 3 and 3A–3B, to lock the components together. The preferred split collet 28 can be made from titanium, stainless steel or cobalt-chromium alloys. Sleeve 16 has bottom 25 received within bore 18. The same locking function is performed by sleeve 16 in the embodiments of FIGS. 6–8 that show a modular distal shaft 30. Alternatively, a solid construction could be employed for the sleeve (not shown), using a super-elastic material that is inherently radially flexible under controlled temperature conditions, e.g., a nickel-titanium alloy such as nitinol. Sleeve 16 has an outer surface 31 that engages bore 18.

The body 14 will now be more particularly described. As shown is FIG. 2A, taken through the region of first or proximal end 15 of body 14, the body has an outer surface 32 with a "generally polygonal" cross-sectional shape, although the polygon is preferably a triangle. Such a shape affords non-tangential contact with the intact bone, in a plane perpendicular to the longitudinal axis of the bone. Together with the tapered contour in the proximal-distal plane, body 14 functions as a three-dimensional wedge. By the term "generally polygonal", it is meant that one or more of the sides of the polygon could be either linear or slightly bowed, in a concave or convex manner. However, substantially linear sides are preferred. The degree to which the sides may be bowed should not defeat the function of the angular corners 34 shown in FIGS. 1, 2, 2A, 2C and 4–10, as well as in FIGS. 11–12 that will be described below.

Figure 13:
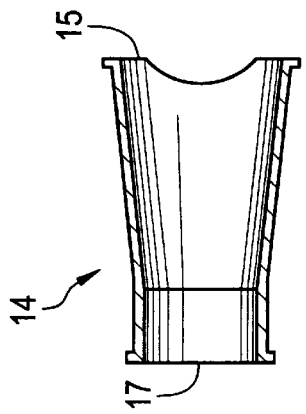
FIG. 13 is a sectional view, taken substantially along lines 13—13 of FIG. 12.
Figure 12:
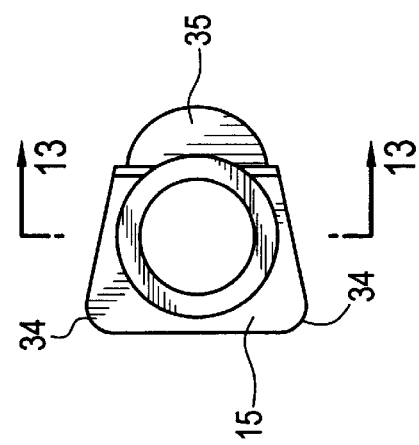
FIG. 12 is a top view of the body component of FIG. 11.
Figure 11:
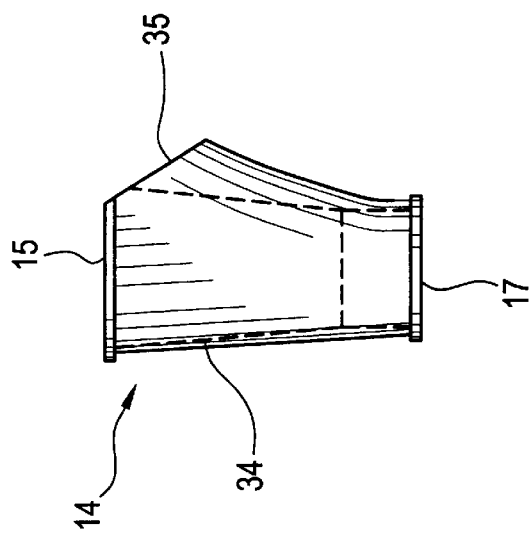
FIG. 11 is an external view of the body of a prosthesis of the invention with a medial osteotomy plane.

The centroid (not shown) of the proximal polygonal cross-sectional shape of body 14 need not coincide with axis A of bore 18. Likewise, the centroid (not shown) of the distal cross-section (FIG. 28) which could be polygonal or preferably round, need not coincide with the axis A of bore 18, although such coincidence is preferred. Neither of the first 15 and second 17 ends of body 14 need be perpendicular to the axis A of bore 18, yet, it is preferred that ends 15, 17 are perpendicular to axis A. As shown in FIGS. 11–13, body 14 has a planar osteotomy surface 35, oriented at a selected angle relative to axis A, such that the distance between the axis A and the edge of the outer surface 32 increases in a direction from the first end of the body toward the second end of the body. The planar surface 35 generally corresponds to the location of an osteotomy cut. Either of the surfaces 15 or 35 could optionally carry a collar member (not shown) that is meant to rest on the end of the bone, where clinically indicated, to help prevent linear subsidence of the body component axially into the bone cavity. As to the function of the cross-sectional shape, however, the body geometry shown in FIGS. 11–13 has the same function as in the other embodiments previously discussed. That is, the corners 34 incise into the bone to provide rotatory stability to the implanted prosthesis 10, while effectively loading the bone.

Reference is now made to the three views of sleeve 16 shown in FIG. 3. An outer surface 31 of sleeve 16 contacts bore 18 and creates a lock between stem 12 and body 14, while an inner bore 36 of the sleeve creates a lock between stem 12 and the body, when axial force is applied to the assembled components. Sleeve 16 is radially flexible about axis A of bore 18, by means of collet 28. As with the first 15 and second 17 ends of body 14, the opposed top 24 and bottom 25 of sleeve 16 need not lie in planes that are parallel to one another, although such is preferred. As shown in of FIG. 3A, sleeve 16 may have either a straight or tapered bore 36. Similarly, the outer surface 31 of sleeve 16 could be tapered or straight. The sleeve may have bore 36 of different diameters correspond to the different outer diameters of the stem 12, respectively. The thickness of the wall defined between the inner diameter of the bore 36 and outer diameter to the surface 31 may be varied to accommodate different corresponding diameter sizes of the stem.

Although a single through-bore 18 is preferred, separate bores (not shown) could be used to receive each of the distal shaft and neck components, as in the case of a modular stem construction contemplated by FIGS. 6–7. In a modular construction, shaft 30 has a free end or distal tip 37 that is received within the medullary canal of the femur, in the case of hip prosthesis 10.

In the top and external views of FIG. 3, top 24 of sleeve 16 has an optional upper shoulder 38 that is spaced from surface 15 of body 14. In FIG. 8 an embodiment is shown wherein the optional shoulder 38 stops the sleeve 16 from falling through the bore 18 in body 14 which is necessary since the bore 18 and outer surface 31 of sleeve 16 are both straight rather than tapered. When the stem 12 is passed through the sleeve 16 the taper connection region 40 adjacent the bottom 20 of neck 22 spreads the collet 28 of sleeve 16 and locks the components together. Shoulder 38 has an underside 42 that abuts the outer periphery of bore 18 and stops the sleeve 16 from falling through the bore 18. Alternatively instead of the shoulder 38 limiting axial motion of the sleeve relative to the bore, the bore could have a counter-sunk inlet (not shown) that would abut the bottom 25 of sleeve 16 and arrest its downward motion in the bore. The leg length could be adjusted by using different height shoulders 38.

Referring to FIGS. 1, 4, 6 and 7–8, neck 22 carries a joint motion surface via tapered connector 44 to which a ball (not shown) may be attached having the acetabular fit needed to ensure proper articulation and total joint tension. Distal shaft 30 could be coated, fluted, slotted or the like. The connection region 40, although shown with a tapered diameter in FIG. 8, as well as in a unitary stem 12 or modular neck 22 and shaft 30 configuration, can also have a straight diameter in the other embodiments described. Region 40 is adjacent a fixed or proximal end 41 of modular shaft component 30 (FIGS. 6–7), which is longitudinally opposed from distal tip 37. End 41 is received within sleeve 16.

Figure 5A:
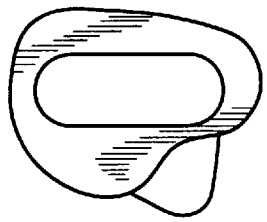
FIG. 5 is a cross-section of the proximal portion of the body of the invention, implanted in a cadaver bone, showing also the cross-section of a representative prior art implant for comparison purposes.
Figure 5B:
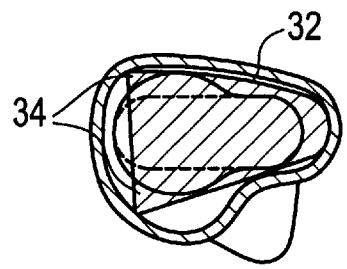

Reference is now made to FIG. 5, showing the preferred triangular proximal cross-sections of the invention versus a representative prior art collar (oval and keyhole shapes) in an actual cadaver bone. Superimposed on the prior keyhole shape is the triangular cross-section of the invention. By contrast, the prior art relies upon circumferential and, ultimately tangential contact with the bone and does not present a multi-axial wedged shape that reaches out and incises into intact bone in the lateral regions of the proximal femoral cavity, as does the present design. This structural difference results in a crucial functional distinction.

Figure 9:
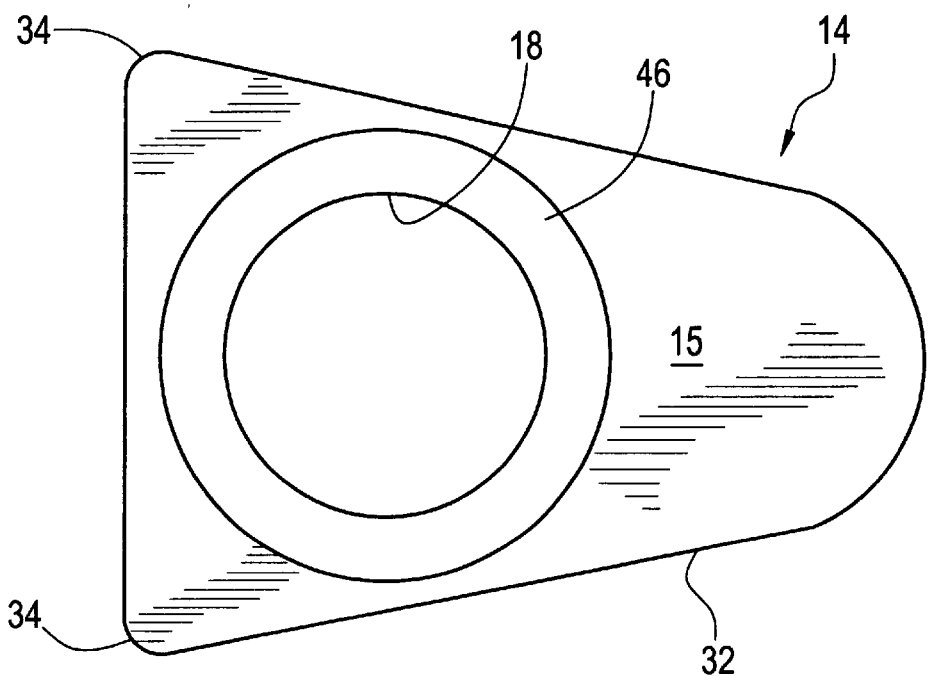
FIG. 9 is a top view of the body component having a generally triangular shape with two sharp corners and a tapered bore.
Figure 10:
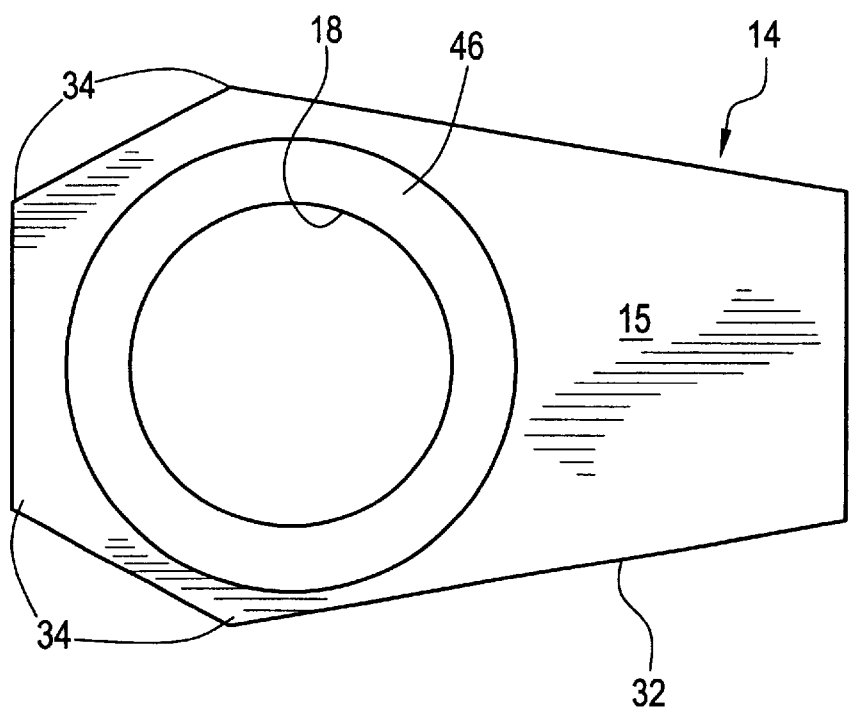
FIG. 10 is a top view of the body component having a generally polygonal shape, i.e., hemi-hexagonal, with sharp corners, and a tapered bore.

In FIGS. 9–10, two preferred polygonal shapes are shown for body 14, taken cross-sectionally in the region of first end 15 adjacent neck 22. In FIG. 12, body 14 has a generally triangular cross-section, with at least two corners 34 on its outer surface 32, whereas, in FIG. 13 there is shown another polygonal shape, i.e., partially hexagonal, which presents such corners 34. The necessity for biting into intact bone, in the case of hip arthroplasty, is most important in the lateral aspect of the femoral cavity, which is less exposed than the medial aspect. This is because the femoral head is resected, exposing the entire proximal medial cavity to the surgeon. This is not so laterally, hence the geometry of the body of the present invention which can reach out and bite into the lateral intact bone. An oval shape does not do this. Bore 18 of body 14 has a tapered portion 46 adjacent the top or proximal end 15, for mating engagement with either sleeve 16 or a tapered stem.

Although the invention has been described with reference to a prosthesis 10 designed for hip arthroplasty, it must be understood that this invention may be used in other types of arthroplasty, e.g., a shoulder joint (not shown), with certain particular adaptations.

The above Description should not be construed as limiting but rather is given for purposes of illustrating the invention. Obviously, persons skilled in the art could make various modifications to the embodiments shown, without departing from the scope of the present invention, as claimed in those claims appended to this Specification.

What is claimed is:

1. A modular orthopedic prosthesis comprising:
   a modular neck component having a protrusion extending distally from the bottom thereof, and another, opposed end for accommodating a joint motion surface;
   a body component including a bore defining at least a first axis and having a generally triangular transverse cross-section with at least two corners of the triangle being angular and defined by intersecting lines of the triangle, whereby said angular corners are adapted to bite into the bone cavity of a patient to prevent rotation of the implanted prosthesis relative to the bone; and
   a radially flexible sleeve having opposed ends, one end being receivable within the said bore and the other end projecting outwardly from the bore; the said protrusion of the neck being received into the said other end of the sleeve; and an outer surface of said sleeve and an inner surface of said bore cooperating to compress said sleeve radially upon insertion of said one end of said sleeve into said bore, whereby the sleeve connects the modular neck component and body together in a fixed position;
   a shaft projecting along said first axis at the side of said prosthesis opposite said modular neck component, the shaft having a distal tip adapted for receipt within the medullary canal of a bone, and the shaft being fixed in its position by the connection of said neck and body components effected by said sleeve.

2. The prosthesis of claim 1, wherein the sleeve further comprises a collet having a bore wherein the neck protrusion is received the neck and collet together further being received within the bore of the body to lock them together.

3. The prosthesis of claim 2, wherein the sleeve further comprises a split collet.

4. The prosthesis of claim 2 wherein the collet has a distal insertion end for receipt within the bore along the first axis and an opposed, proximal end including an annular flange.

5. The prosthesis of claim 2 wherein the annular flange comprises a spacer shoulder having a selected thickness.

6. The prosthesis of claim 1, wherein the neck is attached to the body along the first axis.

7. The prosthesis of 1 wherein said protrusion is attached to the body along the first axis.

8. The prosthesis of claim 1 wherein the sleeve comprises an annular collet made of a super-elastic material.

9. The prosthesis of claim 8 wherein the super-elastic material is nitinol.

10. The prosthesis of claim 1 wherein the bore of the body and an outer surface of the sleeve have interwedging configurations which, when seated together, effect said radial compression of said sleeve whereby to lock the neck component and body together in fixed relative position.

* * * * *